United States Patent [19]

Provin et al.

[11] Patent Number: 4,716,239

[45] Date of Patent: Dec. 29, 1987

[54] NICKEL COMPOSITION SOLUBLE IN HYDROCARBONS

[75] Inventors: Gérard Provin, Ezanville; Alain Forestiere, Vernaison; Dominique Commereuc, Meudon, all of France

[73] Assignee: Institut Francais du Petrole, Rueil-Malmaison, France

[21] Appl. No.: 675,594

[22] Filed: Nov. 28, 1984

[30] Foreign Application Priority Data

Nov. 29, 1983 [FR] France ................................ 83 19183

[51] Int. Cl.$^4$ ............................................. C07F 15/04
[52] U.S. Cl. .................................................... 556/147
[58] Field of Search ........................................ 556/147

[56] References Cited

U.S. PATENT DOCUMENTS

| | | | |
|---|---|---|---|
| 3,133,942 | 5/1964 | Hahl | 556/147 X |
| 3,948,852 | 4/1976 | Rasberger et al. | 556/147 X |
| 4,060,535 | 11/1977 | Cinco | 556/147 |
| 4,248,594 | 2/1981 | Tucker et al. | 556/147 |
| 4,316,851 | 2/1982 | Le Pennec et al. | 556/147 X |

*Primary Examiner*—Helen M. S. Sneed
*Attorney, Agent, or Firm*—Millen & White

[57] ABSTRACT

New nickel composition having substantial solubility in hydrocarbons and prepared by reacting at least one inorganic divalent compound, at least one halogenoacetic acid and at least one ester of the formula $R_1 COO R_2$ wherein $R_1$ is hydrogen or hydrocarbyl and $R_2$ is hydrocarbyl.

The resultant composition can be used in admixture with a hydrocarbylaluminum halide as catalyst for olefin dimerization.

16 Claims, No Drawings

4,716,239

NICKEL COMPOSITION SOLUBLE IN HYDROCARBONS

BACKGROUND OF THE INVENTION

Divalent nickel carboxylates derived from short-chain acids, i.e. having less than 5 carbon atoms, such as acetate, propionate, butyrate and their halogenated derivatives such as chloroacetate, dichloroacetate, trichloroacetate, trifluoroacetate, are known as being practically insoluble in hydrocarbons under normal temperature conditions. On the contrary, the divalent nickel carboxylates derived from long-chain acids, i.e. comprising more than 5 carbon atoms and preferably having a branched chain, such for example as nickel 2-ethyl hexanoate, are soluble in hydrocarbons.

The U.S. Pat. No. 4,316,851 discloses means for solubilizing a halogenoacetate anion linked to nickel, by use of a mixed salt wherein nickel is linked by one of its valencies to the halogenoacetate anion and by the other to the anion of a long-chain carboxylic acid, i.e. comprising at least 5 carbon atoms.

However the presence in a nickel halogenoacetic derivative of an anion derived from a long-chain carboxylic acid results in an additional manufacturing cost and may result in disadvantages when in use. For example, the nickel salts containing the halogenoacetate anion are reacted with alkylaluminum halides in hydrocarbon solution to catalyze the dimerization of olefins in liquid phase; one of the means to remove the inorganic compounds present in the medium at the end of the dimerization step consists of extracting them with a sodium hydroxide aqueous solution; during this step, the presence of the long-chain carboxylate anion, as a result of the surfactant properties of its sodium derivative, leads to the formation of foams, which are detrimental to the phase separation, and also to a poor dispersion of the nickel oxide produced by reaction of the catalyst with sodium hydroxide.

OBJECT OF THE INVENTION

It is therefore an object of the present invention to provide a method for manufacturing a new nickel composition, soluble in hydrocarbons, containing the halogenoacetate anion, said method avoiding the use of a carboxylate anion having more than 5 carbon atoms. An additional object is the provision of compositions produced thereby, and of a process for the dimerization of liquid phase olefins.

SUMMARY OF THE INVENTION

It has been discovered that the interaction of at least one inorganic compound of divalent nickel with a halogenoacetic acid, within an ester a carboxylic acid forms a liquid composition soluble in hydrocarbons. This solubility in hydrocarbons is unexpected since the inorganic nickel derivatives involved, and the nickel halogenoacetates whose formation can be expected, are completely insoluble in hydrocarbons under normal temperature conditions.

The nickel inorganic compound according to the invention is, for example, a carbonate, a bicarbonate, a basic carbonate (hydroxycarbonate), a hydroxide or an oxide.

The halogenoacetic acid is for example monochloroacetic, monofluoroacetic, dichloroacetic, trichloroacetic, difluoroacetic or trifluoroacetic acid.

The esters of carboxylic acids comply with the general formula $R_1COOR_2$ wherein $R_1$ and $R_2$ are hydrocarbyl radicals, $R_1$ being also optionally hydrogen. More particularly $R_1$ and $R_2$ may each consist of a branched or linear alkyl group comprising 1-20 carbon atoms, preferably 1-5 carbon atoms, or an aryl group comprising 6-9 carbon atoms, $R_1$ being also optionally hydrogen. Examples are methyl acetate, methyl formate n-butyl acetate, isobutyl acetate, methyl propionate, isopropyl formate.

The proportion of halogenoacetic acid is 0.1-2 moles, preferably 0.5-1.5 moles per nickel atom involved.

The ester, as above defined, is used in a proportion of 0.1-10 liters of ester and preferably 0.2-2 liters of ester per nickel gram-atom involved.

To the three components mixture, as above defined, a non-halogenated carboxylic acid containing at least three carbon atoms, such as butyric acid, lauric acid, 2-ethyl hexanoic acid, stearic acid, may also be added. But, in constrast with what is disclosed in the U.S. Pat. No. 4,316,851, such addition of acid is not indispensable to obtain the solubility in hydrocarbons and, on the other hand, the acid amount is in a molar ratio acid/nickel lower than 1, preferably 0.1-0.9 mole of carboxylic acid per nickel atom.

A preferred embodiment of the invention comprises introducing, under vigorous stirring, the halogenoacetic acid in the previously formed mixture of the nickel compound with the ester.

The temperature of the mixture ranges from room temperature to the boiling point of the ester under the selected pressure, preferably at reflux and while removing carbon dioxide and water formed during the reaction. The reaction is continued until complete dissolution of the nickel, complete consumption of the free halogenoacetic acid and discontinuation of the water and/or carbon dioxide formation. The optional introduction of non-halogenated carboxylic acid may take place either before the introduction of halogenoacetic acid or at any moment of the reaction, even at the end.

The reaction may be performed in the presence of a hydrocarbon such as pentane, hexane, heptane, octane or their isomers and their mixtures or benzene, toluene, xylenes. The hydrocarbon may then be introduced in variable amount, at the beginning, in the course or at the end of the reaction. The hydrocarbon may optionally help to remove the reaction water.

The invention also concerns catalytic compositions comprising (a) a soluble nickel composition as above described and (b) a hydrocarbylaluminum halide, preferably in a proportion of 1-50 moles per nickel atom, more preferably 2-20 moles per nickel atom.

The invention also concerns the use of the above-mentioned catalytic composition as catalyst for liquid phase olefin dimerization, at a preferred temperature of 0°-60° C.

The olefin is, for example, ethylene, propylene or a butene.

The proportion of catalytic composition is preferably 5-500 parts per million by weight.

EXAMPLES

The following examples illustrate the invention without limiting the scope thereof:

EXAMPLE 1

A mixture of 10 g ($8.10^{-2}$ mole) of nickel basic carbonate $NiCO_3$, $Ni(OH)_2$, $H_2O$ with 150 cc of butyl acetate and 6 cc ($8.10^{-2}$ mole) of trifluoroacetic acid, is brought to reflux for 2 hours, while removing water as it is formed.

A micellar green solution is obtained which can be diluted with heptane in any amount without precipitation.

EXAMPLE 2

Example 1 is repeated but with the further addition of 4.4 g ($5.10^{-2}$ mole) of butyric acid.

The obtained solution, of green colour, may be diluted in any proportion with heptane without precipitation.

EXAMPLE 3

Example 2 is repeated except that trifluoroacetic acid is replaced with $8.10^{-2}$ mole of trichloroacetic acid. The same type of micellar solution which contains the almost entirety of the introduced nickel is obtained. It can be diluted in any proportion with hydrocarbons.

EXAMPLE 4

This example forms no part of the invention and is given to illustrate the necessary use of an ester in order to obtain nickel in solution.

A mixture of 10 g of the same nickel carbonate and 6 cc of trifluoroacetic acid is brought to reflux in 200 cc of hexane. Carbon dioxide evolves quickly while the medium remains completely colorless and an insoluble compound is formed which is identified as nickel bistrifluoroacetate.

EXAMPLE 5

Example 2 is repeated except that butyl acetate is replaced with 150 cc of methyl formate. A green solution is obtained which contains the major part of the introduced nickel.

EXAMPLE 6

The procedure is the same as in Example 2 except that butylacetate is replaced with ethyl butyrate. A green solution is obtained which contains the entirety of the introduced nickel and which can be diluted to any extent with heptane.

EXAMPLE 7

The solution obtained in Example 1 is used for dimerizing butenes.

A system of two reactors of 0.25 liter, arranged in series and adapted for heat regulation, is fed continuously, at 45° C., with: 100 g/h of a $C_4$ hydrocarbon cut containing 72% of n-butenes, 0.1 m M/h of nickel, present as composition of Example 1 dissolved in heptane, and 1.5 m M/h of dichloroethylaluminum dissolved in heptane. In order to remove the inorganic components of the catalyst, the hydrocarbon effluent of the second stage is treated with a 18% by weight sodium hydroxide aqueous solution and is then washed continuously with water, in 2 reactors, arranged in series, each also of a 0.25 liter volume.

No settling difficulty is observed for the phases involved and the recovered hydrocarbon phase is properly demineralized. Nickel oxide, which precipitates by action of the sodium hydroxide solution, is completely dispersed therein and may thus be easily removed from the hydrocarbon phase.

In a comparative example where the mixed salt nickel trifluoroacetate 2-ethyl hexanoate is used in lieu of the composition of Example 2, profused foams are formed during the water washing, which impede a correct settling. In addition, the precipitated nickel oxide is found at the interface between the sodium hydroxide aqueous solution and the hydrocarbon phase, making thus difficult to remove the nickel.

EXAMPLE 8

A reaction system consisting of two serially arranged stages of 9 liters volume, maintained at 40° C. under a pressure of 2 MPa, is continuously fed with 1000 g/h of a cut containing 95% of propylene, 5.5 m M/h of dichloroethyl aluminum dissolved in heptane, and 0.55 m M/h of nickel as the composition of Example 2, dissolved in heptane. Under steady running conditions, the conversion of the first stage is 90.1% and that of all stages together is 96.5%. The effluent is treated with a 20% sodium hydroxide aqueous solution and then with water. A good settling between hydrocarbon and aqueous phases is obtained. Nickel oxide precipitated by action of the sodium hydroxide solution, is completely dispersed therein and may thus be easily removed from the hydrocarbon phase.

EXAMPLE 9

Example 8 is repeated except that the catalytic composition of Example 2 is replaced by that of Example 6. A conversion of 89% is obtained in the first stage and 95.5% in all the stages together. The separation is as good as in Example 8.

What is claimed as the invention is:

1. A nickel liquid reaction product composition, soluble in hydrocarbons, obtained by the process comprising reacting:
   a divalent nickel inorganic compound;
   a halogenoacetic acid;
   and an ester of the general formula $R_1COOR_2$, wherein $R_1$ is hydrogen or $C_{1-4}$-alkyl and $R_2$ is a hydrocarbyl radical.

2. A composition according to claim 1, whose manufacture comprises the use of halogenoacetic acid in a proportion of 0.1-2 moles per nickel atom of the inorganic compound and ester in a proportion of 0.1-10 liters per nickel atom of the inorganic compound.

3. A composition according to claim 1, whose manufacture comprises the use of halogenoacetic acid in a proportion of 0.5-1.5 mole and ester is a proportion of 0.2-2 liters per nickel atom of the inorganic compound.

4. A composition according to claim 1, whose manufacture comprises, as the nickel inorganic compound, a carbonate, bicarbonate, basic carbonate, oxide or hydroxide.

5. A composition according to claim 1, whose manufacture comprises, as the nickel inorganic compound, a nickel basic carbonate.

6. A composition according to claim 1, whose manufacture comprises, as halogenoacetic acid, trifluoroacetic acid.

7. A composition according to claim 1, whose manufacture further comprises the reaction of a non-halogenated carboxylic acid having at least 3 carbon atoms, in a proportion of 0.1-0.9 mole per nickel atom.

8. A composition according to claim 1, wherein $R_2$ is $C_{1-5}$-alkyl.

9. A composition according to claim 1, wherein $R_1$ is hydrogen or $C_{1-3}$-alkyl.

10. A composition according to claim 8, wherein the ester is methyl acetate, methyl formate, n-butyl acetate, isobutyl acetate, methyl propionate, isopropyl formate or ethyl butyrate.

11. A composition according to claim 1, wherein the halogenoacetic acid is monochloroacetic acid, monofluoroacetic acid, dichloroacetic acid, trichloroacetic acid, difluoroacetic acid or trifluoroacetic acid.

12. A process for the production of nickel liquid reaction product compositions, soluble in hydrocarbons, comprising reacting together:
   a divalent nickel inorganic compound;
   a halogenoacetic acid; and
   an ester of the formula $R_1COOR_2$, wherein $R_1$ is hydrogen or a $C_{1-4}$-hydrocarbyl radical and $R_2$ is a hydrocarbyl radical.

13. A process according to claim 12, comprising reacting the halogenoacetic acid in a proportion of 0.1-2 moles per nickel atom of the inorganic compound and reacting the ester in a proportion of 0.1-10 liters per nickel atom of the inorganic compound.

14. A process according to claim 13, wherein the halogenoacetic acid comprises monochloroacetic acid, monofluoroacetic acid, dichloroacetic acid, trichloroacetic acid, difluoroacetic acid or trifluoroacetic acid.

15. A process according to claim 12, further comprising reacting a non-halogenated carboxylic acid having at least three carbon atoms, in a proportion of 0.1-0.9 mole per nickel atom.

16. A process according to claim 12, wherein the ester is methylacetate, methylformate, n-butyl acetate, isobutyl acetate, methylpropionate, isopropylformate or ethylbutyrate.

* * * * *